US011160865B2

(12) United States Patent
Theisinger et al.

(10) Patent No.: US 11,160,865 B2
(45) Date of Patent: *Nov. 2, 2021

(54) LIQUID PHARMACEUTICAL COMPOSITION FOR THE DELIVERY OF ACTIVE INGREDIENTS

(71) Applicants: Bastian Theisinger, Mannheim (DE); Sonja Theisinger, Mannheim (DE); Bernhard Günther, Dossenheim (DE)

(72) Inventors: Bastian Theisinger, Mannheim (DE); Sonja Theisinger, Mannheim (DE); Bernhard Günther, Dossenheim (DE)

(73) Assignee: NOVALIQ GMBH, Heidelberg (DE)

( * ) Notice: Subject to any disclaimer, the term of this patent is extended or adjusted under 35 U.S.C. 154(b) by 239 days.

This patent is subject to a terminal disclaimer.

(21) Appl. No.: 15/945,587

(22) Filed: Apr. 4, 2018

(65) Prior Publication Data

US 2018/0221485 A1  Aug. 9, 2018

Related U.S. Application Data

(63) Continuation of application No. 15/658,187, filed on Jul. 24, 2017, now Pat. No. 9,968,678, which is a continuation of application No. 13/824,048, filed as application No. PCT/EP2011/068141 on Oct. 18, 2011, now Pat. No. 9,757,459.

(30) Foreign Application Priority Data

Oct. 20, 2010 (EP) .................................... 10188242

(51) Int. Cl.
*A61K 47/06* (2006.01)
*A61K 9/00* (2006.01)
*A61K 47/24* (2006.01)

(52) U.S. Cl.
CPC ............ *A61K 47/06* (2013.01); *A61K 9/0019* (2013.01); *A61K 9/0043* (2013.01); *A61K 9/0046* (2013.01); *A61K 9/0048* (2013.01); *A61K 47/24* (2013.01)

(58) Field of Classification Search
None
See application file for complete search history.

(56) References Cited

U.S. PATENT DOCUMENTS

| | | | |
|---|---|---|---|
| 2,616,927 A | 11/1952 | Kauck et al. | |
| 5,077,036 A | 12/1991 | Long | |
| 5,326,566 A | 7/1994 | Parab | |
| 5,336,175 A | 8/1994 | Mames | |
| 5,518,731 A | 5/1996 | Meadows | |
| 5,667,809 A | 9/1997 | Trevino et al. | |
| 5,874,469 A | 2/1999 | Maniar et al. | |
| 5,980,936 A | 11/1999 | Krafft et al. | |
| 5,981,607 A | 11/1999 | Ding | |
| 6,042,845 A | 3/2000 | Sun et al. | |
| 6,060,085 A | 5/2000 | Osborne | |
| 6,113,919 A | 9/2000 | Reiss et al. | |
| 6,159,977 A | 12/2000 | Reeves | |
| 6,177,477 B1 | 1/2001 | George et al. | |
| 6,197,323 B1 | 3/2001 | Georgieff | |
| 6,224,887 B1 | 5/2001 | Samour et al. | |
| 6,262,126 B1 | 7/2001 | Meinert | |
| 6,294,563 B1 | 9/2001 | Garst | |
| 6,372,243 B2 | 4/2002 | Kobuch | |
| 6,391,879 B1 | 5/2002 | Reeves | |
| 6,458,376 B1 | 10/2002 | Meadows | |
| 6,486,212 B2 | 11/2002 | Meinert | |
| 6,730,328 B2 | 5/2004 | Maskiewicz et al. | |
| 7,001,607 B1 | 2/2006 | Menz et al. | |
| 7,026,359 B1 | 4/2006 | Gross | |
| 7,258,869 B1 | 8/2007 | Berry et al. | |
| 7,740,875 B2 | 6/2010 | Dechow | |
| 8,029,977 B2 | 10/2011 | Meinert | |
| 8,222,292 B2 | 7/2012 | Goskonda et al. | |
| 8,470,873 B2 | 6/2013 | Chen | |
| 8,614,178 B2 | 12/2013 | Theisinger et al. | |
| 8,796,340 B2 | 8/2014 | Theisinger et al. | |
| 8,916,157 B2 | 12/2014 | Krause et al. | |

(Continued)

FOREIGN PATENT DOCUMENTS

| EP | 0 089 815 | 9/1983 |
|---|---|---|
| EP | 0593552 | 4/1994 |

(Continued)

OTHER PUBLICATIONS

Lu, H., et al., Journal of Biomedical Optics 19(2): 027001-1-027001-8 (2014). (Year: 2014).*
Ahmed, I. et al., "Disposition of Timolol and Inulin in the Rabbit Eye Following Corneal Versus Non-Corneal Absorption," International Journal of Pharmaceutics, 1987, 38, 9-21.
Baerdemaeker, "Pharmacokinetics in Obese Patients," Continuing Education in Anaesthesia, Critical Care & Pain, 2004, 4, 152-155.
Broniatowski, M. et al., "Langmuir Monolayers Characteristics of Perfluorodecyl)-Alkanes," Journal of Physical Chemistry B, 2004, 108, 13403-13411.
Chemical Book, 5-Fluorouracil, available at <http://www.chemicalbook.com/ChemicalProductProperty_EN_CB8162744.htm>, accessed Mar. 7, 2014, 1 page.

(Continued)

*Primary Examiner* — David J Blanchard
*Assistant Examiner* — Daniel F Coughlin
(74) *Attorney, Agent, or Firm* — Hoxie & Associates LLC

(57) ABSTRACT

The invention provides novel pharmaceutical compositions based on semifluorinated alkanes which are useful as carriers for a broad range of active ingredients. Preferred active ingredients include poorly water-soluble and/or hydrolytically sensitive drug substances. The compositions are designed as suspensions and have superior physical properties which make them highly useful as pharmaceutical delivery systems. The compositions may be administered topically into the eye, or injected via the subcutaneous or intramuscular route. The invention further provides kits comprising such compositions.

22 Claims, 4 Drawing Sheets

(56) References Cited

U.S. PATENT DOCUMENTS

| | | |
|---|---|---|
| 8,986,738 B2 | 3/2015 | Meinert |
| 9,241,900 B2 | 1/2016 | Wilson |
| 9,308,262 B2 | 4/2016 | Günther et al. |
| 9,757,459 B2 | 9/2017 | Theisinger et al. |
| 9,757,460 B2 | 9/2017 | Günther et al. |
| 9,770,508 B2 | 9/2017 | Günther et al. |
| 2002/0128527 A1 | 9/2002 | Meinert |
| 2002/0198266 A1 | 12/2002 | Meinert |
| 2003/0018044 A1 | 1/2003 | Peyman |
| 2003/0027833 A1 | 2/2003 | Cleary et al. |
| 2003/0170194 A1 | 11/2003 | Piotrowiak |
| 2004/0266702 A1 | 12/2004 | Dawson et al. |
| 2005/0079210 A1 | 4/2005 | Gupta |
| 2005/0175541 A1 | 8/2005 | Lanza et al. |
| 2005/0274744 A1 | 12/2005 | Spada et al. |
| 2005/0288196 A1 | 12/2005 | Horn |
| 2006/0153909 A1 | 7/2006 | Motoune et al. |
| 2008/0207537 A1 | 8/2008 | Turner et al. |
| 2008/0234389 A1 | 9/2008 | Mecozzi et al. |
| 2008/0260656 A1 | 10/2008 | Mallard |
| 2010/0006600 A1 | 1/2010 | Dascanio |
| 2010/0008996 A1 | 1/2010 | Meinert |
| 2010/0016814 A1 | 1/2010 | Gokhale et al. |
| 2010/0226997 A1 | 9/2010 | Bowman et al. |
| 2010/0274215 A1 | 10/2010 | Wong et al. |
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2012/0244177 A1 | 9/2012 | Theisinger et al. |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2013/0336557 A1 | 12/2013 | Cruzat et al. |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0186350 A1 | 7/2014 | Ghosh et al. |
| 2014/0369993 A1 | 12/2014 | Günther et al. |
| 2015/0224064 A1 | 8/2015 | Günther et al. |
| 2015/0238605 A1 | 8/2015 | Günther et al. |
| 2016/0101178 A1 | 4/2016 | Wilson |
| 2016/0159902 A1 | 6/2016 | Günther et al. |
| 2016/0243189 A1 | 8/2016 | Gu et al. |
| 2017/0020726 A1 | 1/2017 | Labombarbe et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2017/0216204 A1 | 8/2017 | Theisinger et al. |
| 2018/0360908 A1 | 12/2018 | Beier et al. |

FOREIGN PATENT DOCUMENTS

| | | |
|---|---|---|
| EP | 0 670 159 A1 | 9/1995 |
| EP | 0 965 329 A1 | 12/1999 |
| EP | 0 965 334 A1 | 12/1999 |
| EP | 0 939 655 B1 | 6/2002 |
| EP | 1 152 749 B1 | 4/2006 |
| EP | 2 110 126 A1 | 10/2009 |
| EP | 2 332 525 A1 | 6/2011 |
| EP | 2 335 735 A1 | 6/2011 |
| EP | 2 462 921 | 6/2012 |
| JP | S6452722 | 2/1989 |
| JP | 2000511157 | 8/2000 |
| JP | 2001/158734 | 6/2001 |
| JP | 2008/505177 | 2/2008 |
| JP | 2011/006348 | 1/2011 |
| JP | 2011/024841 A | 2/2011 |
| WO | WO 1995/033447 | 12/1995 |
| WO | WO 96/40052 | 12/1996 |
| WO | WO 97/12852 | 4/1997 |
| WO | WO 00/10531 | 3/2000 |
| WO | WO 00/024376 | 5/2000 |
| WO | WO 00/054588 | 9/2000 |
| WO | WO 02/49631 | 6/2002 |
| WO | WO 2005/099718 | 10/2005 |
| WO | WO 2005/099752 | 10/2005 |
| WO | WO 2005/123035 | 12/2005 |
| WO | WO 2006/007510 | 1/2006 |
| WO | WO 2006/042059 | 4/2006 |
| WO | WO 2006/048242 | 5/2006 |
| WO | WO 2007/052288 | 5/2007 |
| WO | WO 2008/060359 | 5/2008 |
| WO | WO 2008/136034 | 11/2008 |
| WO | WO 2009/013435 | 1/2009 |
| WO | WO 2009/065565 | 5/2009 |
| WO | WO 2010/062394 | 6/2010 |
| WO | WO 2010/146536 | 12/2010 |
| WO | WO 2011/009436 | 1/2011 |
| WO | WO 2011/073134 | 6/2011 |
| WO | WO 2011/113855 | 9/2011 |
| WO | WO 2012/062834 | 5/2012 |
| WO | WO 2012/093113 | 7/2012 |
| WO | WO 2012/121754 | 9/2012 |
| WO | WO 2012/160179 | 11/2012 |
| WO | WO 2012/160180 | 11/2012 |
| WO | WO 2013/110621 | 8/2013 |
| WO | WO 2014/041055 | 4/2014 |
| WO | WO 2014/041071 | 4/2014 |
| WO | WO 2014/154531 | 10/2014 |
| WO | WO 2015/011199 | 1/2015 |
| WO | WO 2016/025560 | 2/2016 |
| WO | WO 2017/210158 | 12/2017 |
| WO | WO 2017/220625 | 12/2017 |
| WO | WO 2018/060282 | 4/2018 |
| WO | WO 2018/114557 | 6/2018 |
| WO | WO 2018/115097 | 6/2018 |

OTHER PUBLICATIONS

Costa Gomes et al., "Solubility of dioxygen in seven fluorinated liquids," Journal of Fluorine Chemistry, 2004, 125, 1325-1329.

Davies, N., "Biopharmaceutical Considerations in Topical Ocular Drug Delivery," Clinical and Experimental Pharmacology and Physiology, 2000, 27, 558-562.

Dembinski, R. et al., "Semi-fluorinated Alkanes as Carriers for Drug Targeting in Acute Respiratory Failure," Experimental Lung Research, 2010, 36, 499-507.

Dias et al., "Solubility of oxygen in liquid perfluorocarbons," Fluid Phase Equilibria, 2004, 222-223:325-330.

Elkeeb, R. et al., "Transungual Drug Delivery: Current Status," International Journal of Pharmaceutics, 2010, 384, 1-8.

English-language machine translation of EP0670159 (A1) issued in U.S. Appl. No. 14/122,025 on Apr. 1, 2015, 10 pages.

Freiburger Dokumentenserver (FreiDok), Albert-Ludwigs-Unversitat Freiburg, retrieved from http://www.freidok.uni-freiburg.de/volltexte/5682/, retrieved on Feb. 5, 2014, 2 pages.

Gayton, J., "Etiology, Prevalence, and Treatment of Dry Eye Disease," Clinical Ophthalmology, 2009, 3, 405-412.

Gerdenitsch, "Emulsions—established and promising drug carriers for parenteral adminstration", International Pharmaceutical Industry, 62-62, retrieved from internet: http://ipimediaworld.com/wp-content/uploads/2012/05/Pages-from-IPI-Volume-2-Issue-1-11.pdf Date Accessed: Jun. 20, 2016.

Griffin, W., "Classification of Surface-Active Agents by 'HLB'," Journal of the Society of Cosmetic Chemists, 1949, 1, 311-326.

Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf [retrieved on Oct. 10, 2011].

Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).

Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.

Holm, R. et al., "A novel excipient, 1-perfluorohexyloctane shows limited utility for the oral delivery of poorly water-soluble drugs," European Journal of Pharmaceutical Sciences, 2011, 42, 416-422.

(56) References Cited

OTHER PUBLICATIONS

International Preliminary Report on Patentability dated Sep. 18, 2012, for International Patent Application PCT/EP2011/053949, 9 Pages.
International Search Report for International Application No. PCT/EP2011/053949 dated Sep. 6, 2011, 5 pages.
International Preliminary Report on Patentability dated Apr. 23, 2013, for International Patent Application PCT/EP2011/068141, 4 Pages.
International Preliminary Report on Patentability for International Application No. PCT/EP2011/069795 dated May 14, 2013, 8 pages.
International Preliminary Report on Patentability for International Application No. PCT/EP2012/050043 dated Jul. 10, 2013, 5 pages.
International Preliminary Report on Patentability for International Application No. PCT/EP2012/059787 dated Nov. 26, 2013, 9 pages.
International Preliminary Report on Patentability for International Application No. PCT/EP2012/059788 dated Nov. 26, 2013, 8 pages.
International Preliminary Report on Patentability for International Application No. PCT/EP2013/051163 dated Jul. 29, 2014, 7 pages.
International Preliminary Report on Patentability dated Mar. 17, 2015, for International Application No. PCT/EP2013/068882, 5 pages.
International Preliminary Report on Patentability dated Mar. 17, 2015, for International Application No. PCT/EP2013/068909, 11 pages.
International Preliminary Report on Patentability dated Jan. 26, 2016, for International Application No. PCT/EP2014/065840, 7 pages.
International Search Report for International Application No. PCT/EP2011/068141 dated Dec. 14, 2011, 2 pages.
International Search Report for International Application No. PCT/EP2011/069795 dated Jan. 16, 2012, 3 pages.
International Search Report for International Application No. PCT/EP2012/050043 dated Apr. 24, 2012, 2 pages.
International Search Report for International Application No. PCT/EP2012/059787 dated Dec. 5, 2012, 4 pages.
International Search Report for International Application No. PCT/EP2012/059788 dated Dec. 3, 2012, 4 pages.
International Search Report for International Application No. PCT/EP2013/051163 dated Mar. 4, 2013, 4 pages.
International Search Report for International Application No. PCT/EP2013/068882 dated Oct. 30, 2013, 4 pages.
International Search Report for International Application No. PCT/EP2013/068909 dated Dec. 5, 2013, 4 pages.
International Search Report for International Application No. PCT/EP2014/065840 dated Oct. 7, 2014, 4 pages.
International Search Report for International Application No. PCT/EP2016/073262 dated Nov. 18, 2016, 5 pages.
International Search Report for International Application No. PCT/EP2016/073263 dated Dec. 23, 2016, 3 pages.
JP 2000511157A, English Machine Translation of the Abstract, Description, and Claims, Espacenet, Date Accessed: Feb. 10, 2016.
JPS6452722, English Machine Translation of the Abstract, Description, and Claims, Espacenet, Date Accessed: Feb. 10, 2016.
Knepp, V. et al., "Stability of Nonaqueous Suspension Formulations of Plasma Derived Factor IX and Recombinant Human Alpha Interferon at Elevated Temperatures," Pharmaceutical Research, 1998, 15 (7), 1090-1095.
Kociok, N., et al, "Influence on Membrane-Mediated Cell Activation by Vesicles of Silicone Oil or Perfluorohexyloctane," Graefe's Archive for Clinical and Experimental Ophthalmology, 2005, 243, 345-358.
Lemp, M., "Management of Dry Eye Disease," The American Journal of Managed Care, 2008, 14 (3), S88-S101.
Mackiewicz, J. et al., "In Vivo Retinal Tolerance of Various Heavy Silicone Oils," Investigative Ophthalmology & Visual Science, 2007, 48 (4), 1873-1883.
Meinert, H. et al., "Semifluorinated Alkanes—A New Class of Compounds with Outstanding Properties for Use in Ophthalmology," European Journal of Ophthalmology, 2000, 10 (3), 189-197.

Meinert, H. et al., "The Use of Semifluorinated Alkanes in Blood-Substitutes," Biomaterials, Artificial Cells, and Immobilization Biotechnology, 1993, 21 (5), 583-595.
Murdan, S., "Enhancing the Nail Permeability of Topically Applied Drugs," Expert Opinion on Drug Delivery, 2008, 5 (11), 1267-1282.
Perry, H., "Dry Eye Disease: Pathophysiology, Classification, and Diagnosis," The American Journal of Managed Care, 2008, 14 (3), S79-S87.
Pinarci, E. et al., "Intraocular Gas Application in the Diagnosis and Treatment of Valsalva Retiopathy in Case with Premacular Hemorrhage," XP002625604, Retina-Vitreus, 2009, 17 (2), 153-155, (Abstract only).
Plassmann, M. et al., "Trace Analytical Methods for Semifluorinated n-Alkanes in Snow, Soil, and Air," Analytical Chemistry, 2010, 82 (11), 4551-4557.
Plassmann, M. et al., "Theoretical and Experimental Simulation of the Fate of Semifluorinated n-Alkanes During Snowmelt," Environmental Science & Technology, 2010, 44(17), 6692-6697.
Rosca-Casian, O. et al., "Antifungal Activity of *Aloe vera* Leaves," Fitoterapia, 2007, 28, 219-222.
Rosenberg, A., "Effects of Protein Aggregates: An Immunologic Perspective," The AAPS Journal, 2006, 8 (3), E501-E507.
Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, 2003, 19:4889-4894.
Stevenson, C., "Characterization of Protein and Peptide Stability and Solubility in Non-Aqueous Solvents," Current Pharmaceutical Biotechnology, 2000, 1, 165-182.
Wong, D. et al., "Perfluorocarbons and Semifluorinated Alkanes," Seminars in Ophthalmology, 2000, 15 (1), 25-35.
Ujiie et al., "Successful Treatment of Nail Lichen Planus with Topical Tacrolimus", Department of Dermatology, 2009.
Zakeri et al., "Topical calcipotriol therapy in nail psoriasis", A study of 24 cases, Dermatology Online Journal, 2005.
Zhang et al., "Surface micelles of semifluorinated alkanes in Langmuir-Blodgett monolayers," Phys. Chem. Chem. Phys., 2004, 6:1566-1569.
Barata-Vallejo et al., "(Me3Si)3SiH-Mediated Intermolecular Radical Perfluoroalkylation Reactions of Olefins in Water," J. Org. Chem., 2010, 75:6141-6148.
Bardin et al., "Long-Range Nanometer-Scale Organization of Semifluorinated Alkane Monolayers at the Air/Water Interface," Langmuir, 2011, 27:13497-13505.
Blackie et al., "MGD: Getting to the Root Cause of Dry Eye", Review of Optometry, 2012, pp. 1-12.
Chao, W. et al., "Report of the Inaugural Meeting of the TFOS i2 = initiating innovation Series: Targeting the Unmet Need for Dry Eye Treatment," (London, United Kingdom, Mar. 21, 2015) Accepted Manuscript, Accepted Date: Nov. 11, 2015, 94 pages.
Chhadva et al., "Meibomian Gland Disease the Role of Gland Dysfunction in Dry Eye Disease," Ophthalmology (2017) 124(11 Supplement): S20-S26.
Dutescu, R.M. et al., "Semifluorinated alkanes as a liquid drug carrier system for topical ocular drug delivery," European Journal of Pharmaceutics and Biopharmaceutics, 2014, pp. 123-128.
Gehlsen. U., et al., "Cyclosporine A using F4H5 as liquid drug carrier is effective in treating experimental dry-eye disease," Investigative Ophthalmology & Visual Science, 2015, 56(7):319, Abstract Only (2 pages).
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.
Gehlsen, U., et al., "Omega-3 Fatty Acids Using F6H8-Carrier as Topical Therapy in Experimental Dry-Eye Disease," Investigative Ophthalmology & Visual Science, 2016, 57:417, Abstract Only (1 page).
German, E.J., et al., "Reality of drop size from multi-dose eye drop bottles: is it cause for concern?" Eye, 1999, 13:93-100.
Gopal et al., "Use of intravitreal injection of triamcinolone acetonide in the treatment of age-related macular degeneration," Indian J Ophthalmol., 2007, 55(6):431-435, (8 pages).

(56) References Cited

OTHER PUBLICATIONS

International Preliminary Report on Patentability dated Dec. 25, 2018, for International Application No. PCT/EP2017/065163, 6 pages.
International Preliminary Report on Patentability dated Mar. 26, 2019, for International Application No. PCT/EP2017/073697, 7 pages.
International Preliminary Report on Patentability dated Mar. 26, 2019, for International Application No. PCT/EP2017/074079, 7 pages.
International Preliminary Report on Patentability dated Apr. 2, 2019, for International Application No. PCT/EP2017/074545, 7 pages.
International Preliminary Report on Patentability dated Jun. 25, 2019, for International Application No. PCT/EP2017/082739, 7 pages.
International Search Report for International Application No. PCT/EP2017/065163, dated Aug. 8, 2017, 3 pages.
International Search Report for International Application No. PCT/EP2017/073697 dated Nov. 6, 2017, 4 pages.
International Search Report for International Application No. PCT/EP2017/074079 dated Dec. 22, 2017, 4 pages.
International Search Report for International Application No. PCT/EP2017/074545 dated Nov. 28, 2017, 3 pages.
International Search Report for International Application No. PCT/EP2017/082739 dated Mar. 6, 2018, 3 pages.
International Search Report for International Application No. PCT/EP2017/083770 (revised version) dated Jul. 6, 2018, 4 pages.
International Search Report and Written Opinion for International Application No. PCT/EP2017/083770 dated Jul. 6, 2018, 14 pages.
International Search Report for International Application No. PCT/EP2019/055149 dated May 27, 2019, 4 pages.
Ishizaki et al., "Treatment of Diabetic Retinopathy", Forum: Complication, Practice, 2009, 26(5): 474-476 (3 pages).
Jonas et al., "Intravitreal triamcinolone acetonide for exudative age-related macular degeneration," Br J Ophthalmol, 2003, 87:462-468.
Joussen et al., "The concept of heavy tamponades—chances and limitations," Graefes Arch Exp Ophthalmol, 2008, 246:1217-1224.
Lallemand et al., "Cyclosporine A delivery to the eye: a pharmaceutical challenge," European Journal of Pharmaceutics and Biopharmaceutics, 2003, 56(3):307-318, Abstract Only (1 page).
Kaercher et al., "NovaTears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.
Lin, H. et al., "Dry eye disease: A review of diagnostic approaches and treatments," Saudi Journal of Ophthalmology, 2014, 28:173-181.

Messmer, E.M., "The Pathophysiology, Diagnosis, and Treatment of Dry Eye Disease," (2015) Deutsches Arzteblatt International, 112(5):71-82.
O'Rourke, M. et al., "Enhancing Delivery of Topical Ocular Drops," Cataract & Refractive Surgery Today Europe, 2016, 2 pages.
Pflugfelder et al., "Treatment of Blepharitis: Recent Clinical Trials," 2014, 12(4):273-284, Abstract Only (2 pages).
Pflugfelder et al., "The Pathophysiology of Dry Eye Disease What We Know and Future Directions for Research," Ophthalmology (2017) 124(11 Supplement): S4-S13.
Sall, K. et al. "Two Multicenter, Randomized Studies of the Efficacy and Safety of Cyclosporine Ophthalmic Emulsion in Moderate to Severe Dry Eye Disease," Ophthalmology, 2000, 107(4):631-639.
Sato et al., "Vitrectomy and Intraocular Lens Implantation for Cytomegalovirus Retinitis in a Patient with Acquired Immunodeficiency Syndrome," Presented by Medical Online, New Ophthalmology, 1999, 16(7): 995-998 (4 pages).
Schnetler et al., "Lipid composition of human meibum: a review," S Afr Optom, 2013, 72(2), 86-93.
Spöler et al., "Towards a New in vitro Model of Dry Eye: The ex vivo Eye Irritation Test," Developments in Ophthalmology, 2010, 45, 93-107.
Steven, P. et al. "Semifluorinated Alkane Eye Drops for Treatment of Dry Eye Disease—A Prospective, Multicenter Noninterventional Study" Journal of Ocular Pharmacology and Therapeutics (2015) vol. 31, No. 8, pp. 498-503.
Steven et al., "Semifluorinated Alkane Eye Drops for Treatment of Dry Eye Disease Due to Meibomian Gland Disease," Journal of Ocular Pharmacology and Therapeutics, 2017, 33(9):1-8.
Steven, P. et al. "Semifluorinated Alkane Eye Drops for Treatment of Dry Eye Disease a Prospective, Multicenter Noninterventional Study," Investigative Ophthalmology & Visual Science, 2015, 56:4493, Abstract Only (1 page).
Tamura et al., "Tacrolimus is a class II low-solubility high-permeability drug: The effect of P-glycoprotein efflux on regional permeability of tacrolimus in rats," Journal of Pharmaceutical Sciences, 2002, 91(3):719-729 (Abstract Only), 1 page.
Tiffany, J.M., "Individual Variations in Human Meibomian Composition," Exp. Eye Res., 1978, 27, 289-300.
Troiano et al., "Effect of Hypotonic .4% Hyaluronic Acid Drops in Dry Eye Patients: A Cross-Study", Cornea 27(10): 1126-1130, 1 page (Abstract Only).
"What is retinal vitrectomy?" Presented by: Medical Online, Obesity and Diabetes Mellitus, 2005, 4(2): 284-286 (3 pages).
Wang, W., "Lyophilization and Development of Solid Protein Pharmaceuticals," International Journal of Pharmaceutics, 2000, 203:1-60.
Wirta, David L. et al., "A Clinical Phase II Study to Assess Efficacy, Safety and Tolerability of Waterfree Cyclosporine Formulation for the Treatment of Dry Eye Disease," *Ophthalmology* 126:792-800 (2019).
Xalatan, Latanoprost Ophthalmic Solution, 50 µg/mL Prostaglandin $F_{2\alpha}$ analogue, Product Monograph, Jul. 21, 2014, 30 pages.

\* cited by examiner

LIQUID PHARMACEUTICAL COMPOSITION FOR THE DELIVERY OF ACTIVE INGREDIENTS

CROSS REFERENCE TO RELATED APPLICATIONS

This application is a continuation of U.S. application Ser. No. 15/658,187, filed on Jul. 24, 2017, which is a continuation of U.S. application Ser. No. 13/824,048, filed on Mar. 15, 2013, which is a National Stage Entry under 35 U.S.C. § 371 claiming benefit of PCT Application No. PCT/EP2011/068141, filed on Oct. 18, 2011, which claims priority from European Application No. 10188242.1, filed Oct. 20, 2010, the contents of each of which are hereby incorporated by reference in their entireties.

DESCRIPTION

Background

The present invention relates to pharmaceutical compositions in liquid form which are suitable for the delivery of active ingredients using various routes of administration, in particular injection or topical administration into the nose, an ear, or an eye of a patient.

Pharmaceutical compositions in liquid form represent one of the preferred types of drug formulations. In the context of oral pharmacotherapy, liquid formulations are important for patients who have difficulties swallowing tablets, capsules or other solid dosage forms, such as children or elderly patients, or when substantial dosing flexibility is required. Certain topical routes of administration, such as nasal, otic, or ophthalmic administration, typically require the liquid form in order to provide for an efficient delivery of the active ingredient and a patient-friendly mode of use. Moreover, injectable drug products are mostly in liquid form as the injection or infusion of liquids is particularly convenient and flexible compared to other parenteral dosage forms.

The most simple type of liquid formulation is a solution, such as an aqueous solution of the active pharmaceutical ingredient. In certain cases, however, the development of a more complex formulation such as a suspension may be considered.

For example, if a drug substance is very poorly soluble in aqueous or other biocompatible solvent systems, or if it is hydrolytically labile, a simple solution may not be feasible or represent the best choice. Another occasional motivation to formulate a drug suspension is in order to achieve a prolonged pharmacological effect by slow dissolution and uptake of the active ingredient.

Examples of pharmaceutical suspensions for nasal use include Avamys® (active ingredient: fluticasone furoate), Nasonex® (active ingredient: mometasone furoate), and Pulmicort® Topinasal (active ingredient: budesonide). An ophthalmic suspension that has reached the market stage is, for example, Livocab® (active ingredient: levocabastine). Among the commercial suspension formulations for injection are Humalog® (active ingredient: insulin lispro), Tardocillin® for injection (active ingredient: benzathine benzylpenicillin), as well as most vaccines.

Common problems associated with pharmaceutical suspensions are usually related to physical stability issues, potential irritability, and/or manufacturing challenges. Obviously, suspensions are prone to physical changes of various types, all of which may have impact on drug product quality and performance.

For example, suspended particles may flotate or sediment, depending on their density relative to that of the liquid phase in which they are dispersed. Along with flotation or sedimentation, the suspended particles may aggregate, and depending on the forces by which the particles attract each other, the aggregates thus formed may be rather difficult to resuspend. A further problem is that in suspensions having non-uniform particle sizes there is a tendency for smaller particles to gradually dissolve, whereas larger particles grow through the deposition of dissolved material onto their surfaces (Ostwald ripening). In result, the particle size distribution of a suspension may become broader over time. Particles which grow beyond a certain size may be unsuitable for the intended use; for example, they may occlude an injection cannula or, in case of ophthalmic administration, irritate or even damage the ocular surface.

In general, suspensions of particles have a somewhat higher risk of irritating or damaging certain issues simply by their physical presence. This is true for parenteral injection where suspended particles would bring about the risk of embolic events in the vasculature in case of injection into the bloodstream, for which reason suspensions for intravenous use are normally discouraged, unless it can be assured that all particles are in the low micron or submicron size range and thus not embolic. But also for intradermal, subcutaneous or intramuscular injection it has been found that suspended particles above a certain particle size may lead to some—typically mild—irritation at the injection site, especially of the injected amount of material is relatively large.

Neither is it straightforward to manufacture a pharmaceutical suspension in a highly reproducible manner as is required in particular for non-oral products. If the particle size and the distribution thereof is critical, which is likely in the case of a parenteral suspension, but to some degree also for an ophthalmic suspension, significant process engineering efforts may be required in order to ensure the reproducibility of the physical properties of the formulation. Moreover, if the product is required to be sterile, which is always the case for an injectable or ophthalmic product, heat sterilisation will normally be extremely difficult in view of the major physical changes which the product undergoes during heating, and sterile filtration which is typically performed with products that cannot be heat sterilised will be generally unfeasible. The remaining options include aseptic processing, which is technically complex and challenging, and gamma sterilisation, which may be feasible depending on the chemical stability of the drug substance and of the excipients.

Drug products for the treatment of ophthalmic diseases or conditions are mostly formulated as liquid compositions for local administration. Four ophthalmic target sites for drugs may be differentiated: (a) the conjunctiva, the eye lids, and other structures of the front of the eye; (b) the cornea; (c) the anterior and posterior chamber and their associated structures; and (d) the vitreous cavity (NM Davies, Clin. Exper. Pharmacol. Physiol. 27, 558-562, 2000). Except for the vitreous cavity or body, these targets may be reasonably reached by many therapeutic compounds when administered as eye drops or ointments. In contrast, if the vitreous body is the target, it may be difficult to obtain therapeutic drug concentrations after local topical administration, and systemic or intravitreal administration are typically preferred. For the other targets, the benefits of non-invasive local administration are similar to other topical routes, in particular in that it provides an opportunity to achieve therapeutic drug concentrations at the site of action while minimising the amount of drug in the systemic circulation.

At the same time, achieving local bioavailability of a drug at an ophthalmic target site after topical administration is complicated by several anatomical and physiological factors. A requirement for effective delivery is that a drug formulation introduced to the pre-ocular area must be retained at this site for a sufficient time in order to allow for the uptake of the drug by the respective tissues. A problem of this route of administration is that the normal amount of liquid (tear fluid) present in this region is about 7 µl, most of which resides in the conjunctival sac, while some covers the cornea. The addition of fluid is possible, but probably the holding capacity of the front of an eye is limited to about 30 µl (NM Davies, ibid.). Considering the fact that aqueous eye drops usually have a volume in the region of 50 µl per drop, this illustrates that large fractions of administered drug will normally be lost immediately upon administration through spillage or overflow. Subsequently, drug will be eliminated from the site of administration via the continuous physiological turnover of tear fluid, which occurs at a rate of approx. 1 µl—or about 16%—per minute. These two rapid clearance mechanisms can make the effective local delivery of those drugs rather challenging which are taken up only slowly.

If the target site is the cornea itself, or the anterior or posterior chamber, intraocular absorption from the site of administration at the front of the eye is required. It is believed that the major route of absorption into the eye is through the cornea (I Ahmed, Int. J. Pharm. 38, 9-21, 1987). As the cornea is rather small in its surface area and poorly permeable in comparison with the vascularised conjunctiva, the absorption into the eye is generally not very efficient and leads to intraocular bioavailabilities in the range of only 1-10%. The poor permeability results from the structure of the cornea, which in essence comprises three layers: the outer epithelium, the stroma, and the inner endothelium. Due to the hydrophilic nature of the stroma and the lipophilic epithelial layers, the cornea presents an effective diffusion barrier to both lipophilic and hydrophilic compounds.

Nevertheless, topical ophthalmic delivery, while not highly efficient in absolute terms, is still relatively effective for many small molecular drugs, and acceptable to patients in terms of convenience. As mentioned, most ophthalmic drug products are presented as eye drops or ointments for topical administration. While most of the eye drop formulations are aqueous solutions, the properties of certain drug substances, in particular in terms of solubility and/or hydrolytic instability, present substantial challenges for this type of formulation, so that ophthalmic suspensions remain to be an important alternative to solutions, in spite of their problems as discussed above.

As an alternative to aqueous preparations, oily eye drops may be formulated if the respective drug substance is poorly water-soluble or prone to hydrolytic degradation. However, one of the major disadvantages of all oil-based formulations for ophthalmic administration is that they inherently have a negative impact on vision. Whether used as oily solutions or oil-in-water emulsions, they exhibit a refractive index which differs substantially from that of physiological tear fluid, which leads to visual disturbances and blurring.

Moreover, oil-based formulations do not readily mix with tear fluid to form a homogenous liquid phase. Oily solutions are altogether immiscible with the aqueous tear fluid, and the exact fate of an emulsion mixed with tear fluid in a physiological setting is not completely predictable.

Oil-in-water emulsions of poorly water-soluble drugs like ciclosporin further exhibit the disadvantage that they have a limited drug load capacity. While the active ingredient may have some solubility in the oil phase, this phase is only dispersed in the coherent aqueous phase of the emulsion so that the maximum overall drug concentration in the formulation is very limited.

In contrast to single phase systems such as aqueous or oily solutions, oil-in-water emulsions are also more complex and difficult to manufacture, especially in sterile form. Frequently, emulsions are not readily sterilisable by thermal treatment without negative impact on the physical properties of the emulsion. On the other hand, aseptic processing is complex, costly, and is associated with higher risks of failure, i.e. microbial contamination of the product.

Furthermore, oil-in-water emulsions are like aqueous solutions prone to microbial contamination during use. If they were to be presented in multi-dose containers which are in principle more cost-efficient and convenient for patients than single-use vials, they would have to be preserved in order to ensure their microbiological quality. At the same time, preservatives which can be used in ophthalmic formulations are potentially damaging to the eye, in particular to the ocular surface, and should be avoided whenever possible.

As another alternative to aqueous liquid carriers which are problematic for water-sensitive drug substances, U.S. Pat. No. 6,458,376 proposes eye drops on the basis of non-aqueous liquid perfluorocarbons. At least some of the preferred perfluorocarbons are presented as biocompatible and non-irritating to the eye. The compositions are formulated as suspensions, in particular of polymeric carrier particles which include the drug substance and which are capable of releasing the drug slowly over an extended period of time. Moreover, the compositions may comprise a surfactant such as a non-ionic ethoxylated alcohol or sorbitan. The surfactant functions as a suspension stabiliser and prevents aggregation.

However, it has been found by the present inventors that these drug suspensions in perfluorocarbons suffer from various disadvantages. If formulated without surfactant, they tend to separate (by flotation, or sometimes by sedimentation) very rapidly, and lead to substantial particle aggregation. At the same time, the settled suspensions are very difficult to redisperse by shaking alone. These poor physical suspension properties would seriously impact their usefulness as eye drops. Not only is vigorous shaking and the need for rapid administration before the suspension separates again very inconvenient to patients; poor suspension properties are also associated with the risk of substantial dosing errors. On the other hand, surfactants, which are potentially irritating to the eye and whose use in ophthalmic preparations should be avoided or limited to a low level, are not very effective in stabilising perfluorocarbon suspensions. The incorporation of high amounts of surfactant which may achieve a better stabilisation of the suspension system is physiologically undesirable.

In the context of aerosol delivery of lung surfactant, WO 2005/099718 mentions that semifluorinated alkanes such as perfluorooctylethane or perfluorohexyldecane may be used as liquid carriers of surfactant substitutes, for example native or synthetic phospholipids. The document is silent about the delivery of poorly soluble or chemically instable drug substances, let alone for the purpose of topical administration to the nose or eye, or by injection. Neither does it disclose any other systems beyond colloidal solutions of surfactants.

There is a need for further improvements in the formulation of poorly-soluble or water-sensitive drugs. In particular, there is a need for liquid drug formulations which are suitable for the ophthalmic, injectable, and/or other routes of administration and which do not possess one or more of the disadvantages of prior art compositions. There is also a need for improved suspension formulations which are physically stable and easy to handle, as well as improved non-aqueous formulations for hydrolytically sensitive drug substances.

It is therefore an object of the present invention to provide a novel pharmaceutical composition which is useful for the delivery of poorly-soluble and/or water-sensitive drug substances. Another object is to provide improved formulations for topical ophthalmic delivery which overcome one or more disadvantages of known formulations. It is also an object to provide further improved composition which may be delivered via the injectable route. Moreover, it is an object to provide pharmaceutical suspensions with improved suspension properties. A further object is to provide improved non-aqueous liquid formulations which overcome the limitations of presently known formulations. Further objects of the invention will become clear on the basis of the following description, examples, and patent claims.

SUMMARY OF THE INVENTION

The present invention provides a pharmaceutical composition which is in the form of a suspension and comprises particles of an active ingredient and a liquid vehicle. The vehicle is characterised in that it comprises a semifluorinated alkane.

The active ingredient which is suspended in the vehicle is preferably selected from drug substances which are poorly water-soluble, or sensitive to hydrolytic degradation, or both. The active ingredient is present in a therapeutically effective amount.

The composition of the invention is particularly suitable for the delivery of such preferred drug substances via the topical route of administration, in particular by topical administration to the eye or nose of a patient. It is also useful as an injectable medicine.

It has been found by the inventors that the composition of the invention surprisingly overcomes several drawbacks of previously known aqueous and non-aqueous suspension formulation. In particular, it does not easily agglomerate, and it is readily redispersed homogeneously by simple shaking. Moreover, these advantageous physical properties which allow convenient administration and ensure precise and reproducible dosing are typically achieved without the incorporation of surfactants, or with very low surfactant levels which are unlikely to irritate the eye, nose, or the site of injection.

DETAILED DESCRIPTION OF THE INVENTION

Figure 1:
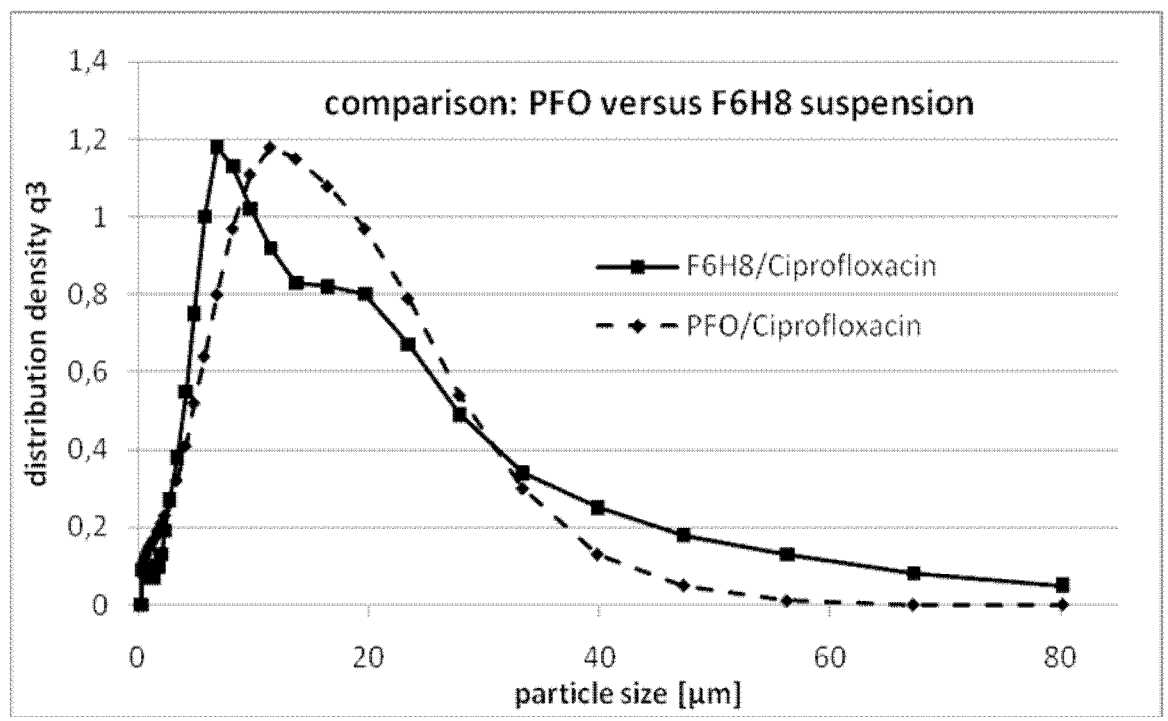
FIG. 1: Particle size distributions of suspensions of ciprofloxacin in F6H8 and PFO.

In a first aspect, the present invention provides a pharmaceutical composition which is in the form of a suspension and comprises particles of an active ingredient, which is present in a therapeutically effective amount, and a liquid vehicle. The vehicle is characterised in that it comprises a semifluorinated alkane of the formula RFRH, wherein RF is a linear perfluorinated hydrocarbon segment with 3 to 10 carbon atoms and wherein RH is a linear alkyl group with 3 to 10 carbon atoms.

As used herein, a pharmaceutical composition is a composition comprising at least one pharmacologically active ingredient or diagnostic agent in combination with at least one pharmaceutical excipient. A therapeutically effective amount refers to a dose, concentration or strength which is useful for producing a desired pharmacological effect.

A suspension may be defined as a type of a dispersion, i.e. a system having at least one continuous (or coherent) phase and at least one discontinuous (or inner) phase which is dispersed in the continuous phase. In a suspension, the dispersed phase is in the solid state. The suspensions useful for practising the invention are liquids, at least at physiological temperature, which means that the continuous phase is a liquid. Typically, the suspensions are also liquid at room temperature.

Some of the key advantages of the present invention are brought about by the presence of a semifluorinated alkane in the composition, functioning as a liquid suspension vehicle. Semifluorinated alkanes are linear or branched alkanes some of whose hydrogen atoms have been replaced by fluorine. In the semifluorinated alkanes (SFA's) used in the present invention, one linear non-fluorinated hydrocarbon segment and one linear perfluorinated hydrocarbon segment are present, each having from 3 to 10 carbon atoms. These compounds thus follow the general formula $F(CF_2)_n(CH_2)_mH$, wherein n and m are independently selected from the range of 3 to 10.

A nomenclature which is frequently used for SFA's designates a perfluorated hydrocarbon segment as RF and a non-fluorinated segment as RH. Alternatively, the compounds may be referred to as FnHm and FnHm, respectively, wherein F means a perfluorated hydrocarbon segment, H means a non-fluorinated segment. Again, n and m define the number of carbon atoms of the respective segment. For example, F3H3 is used for perfluoropropylpropane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

SFA's which are useful in the context of the present invention are also described in EP-A 965 334, EP-A 965329 and EP-A 2110126, the disclosure of which documents is incorporated herein by reference.

Preferred SFA's include in particular the compounds F4H5 (1-perfluorobutylpentane), F4H6 (1-perfluorobutylhexane), F6H4 (1-perfluorohexylbutane), F6H6 (1-perfluorohexylhexane), F6H8 (1-perfluorohexyloctane), and F6H10 (1-perfluorohexyldecane). Particularly preferred for carrying out the invention are F4H5, F4H6, F6H6 and F6H8. In another particularly preferred embodiment, the composition of the invention comprises F6H8.

Optionally, the composition may comprise more than one SFA. It may be useful to combine SFA's, for example, in order to achieve a particular target property such as a certain density or viscosity. If a mixture of SFA's is used, it is furthermore preferred that the mixture comprises at least one of F4H5, F4H6, F6H4, F6H6, F6H8, and F6H10, and in particular one of F4H5, F4H6, F6H6 and F6H8. In another embodiment, the mixture comprises at least two members selected from F4H5, F4H6, F6H4, F6H6, F6H8, and F6H10, and in particular at least two members selected from F4H5, F6H6 and F6H8.

Liquid SFA's are chemically and physiologically inert, colourless and stable. Their typical densities range from 1.1 to 1.7 g/cm$^3$, and their surface tension may be as low as 19 mN/m. SFA's of the RFRH type are insoluble in water but also somewhat amphiphilic, with increasing lipophilicity correlating with an increasing size of the non-fluorinated segment.

Liquid SFA's of the RFRH type are being used commercially for unfolding and reapplying a retina, for long-term tamponade as vitreous humor substitute (H. Meinert et al., European Journal of Ophthalmology, Vol. 10(3), pp. 189-197, 2000), and as wash-out solutions for residual silicon oil after vitreo-retinal surgery. Experimentally, they have also been used as blood substitutes (H. Meinert et al., Biomaterials, Artificial Cells, and Immobilization Biotechnology, Vol. 21(5), pp. 583-95, 1993). These applications have established SFA's as physiologically well tolerated compounds. On the other hand, SFA's have not been used as excipients in approved drug products as of today.

It has been found by the inventors that SFA's are particularly suitable as carriers, vehicles or excipients in ophthalmic compositions for topical administration. This is based on the fact that SFA's are capable of dissolving many poorly water-soluble compounds which are of interest in ophthalmology, but also on the discovery that they are unexpectedly well-tolerated by the eye, as shown in preclinical testing. This is very surprising as organic or non-aqueous solvents, perhaps with the exception of oily compounds, are typically very irritating or even highly damaging when administered topically to an eye.

Compared to oily carriers or vehicles in ophthalmic compositions for topical use, SFA's exhibit a refractive index which is much better compatible with the aim of a minimally affected vision: While oily preparation lead to a blurry vision and can therefore not be administered in any situation in which the patient needs a clear vision, SFA's cause little or no blurring.

TABLE 1

| SFA | Refractive index |
|---|---|
| F4H4 | 1,308 |
| F4H5 | 1,3204 |
| F4H6 | 1,334 |
| F4H7 | 1,3357 |
| F4H8 | 1,348 |
| F6H4 | 1,306 |
| F6H6 | 1,3224 |
| F6H7 | 1,3366 |
| F6H8 | 1,3432 |
| F6H9 | 1,3494 |

By illustration, the refractive index of tear fluid is close to that of water, i.e. 1.333 at room temperature (RT). Oils typically have a substantially higher refractive index such as about 1.46 (peanut oil), 1.47 (sesame oil), or 1.48 (castor oil). In contrast, the inventors have determined the refractive indices of various SFA's of interest to be in the region of 1.29 to 1.35, i.e. much closer to that of water. In one of the specific embodiments, the invention is therefore practised with an SFA whose refractive index is from 1.29 to 1.35, and in particular from about 1.30 to about 1.35 at 20° C. The refractive index for selected SFA's is shown in table 1.

Compared to the perfluorocarbons proposed as vehicles for ophthalmic medicines in e. g. U.S. Pat. Nos. 5,518,731 and 6,458,376, the SFA's provided by the present invention allow the formulation of liquid suspension with superior properties. It has been found by the inventors that when perfluorinated compounds are used as liquid vehicles, the suspensions tend to separate very rapidly by flotation of the dispersed phase, or by its sedimentation, depending on the relative densities of the dispersed phase and of the continuous phase. This is accompanied by a rapid formation of particle aggregates which may be dense and poorly redispersible. Rapid flotation or sedimentation makes precise and reproducible dosing very challenging, if not impossible. For example, if an ophthalmic suspension settles very rapidly after shaking, the first dosing from a full container, if not withdrawn immediately upon shaking, will contain a lower-than-intended number of drug particles, unless the container is held upside down, in which case more than the intended quantity of drug particles will be dispensed. When the same container is nearly empty and the last doses are dispensed, the drug dose withdrawn per volume will be too high if it was low in the beginning, and vice versa.

Moreover, aggregates may easily obstruct the dispensing channels or openings of containers and thereby lead to erroneous dosings. If dispensed from the container, they may cause irritation of the conjunctiva or of the cornea, depending on their size, shape and hardness.

In contrast, the SFA-based suspensions according to the invention remain finely dispersed and homogeneous. If flotation or sedimentation takes place, it occurs slowly, leaving sufficient time for the patient to withdraw a dose after shaking the container. The formation of large aggregates is not observed. After flotation or sedimentation, the drug particles are easily redispersed by gentle shaking, and appear to largely retain their original particle size distribution.

These unexpected properties of SFA-based suspensions result in superior pharmaceutical quality and performance characteristics. The level of convenience to the patient and/or health care provider is greatly increased. More importantly, the dosing accuracy, i.e. precision and reproducibility of dosing, is greatly improved over other types of pharmaceutical suspensions. This will bring about a more reliable therapeutic effect and a reduced risk of adverse effects which result from overdosing.

The superior physical properties of the suspensions according to the invention render these compositions particularly useful for topical administration to the eye of a patient. However, similar benefits are also achieved when the suspensions are administered nasally, into an ear, or parenterally by injection. Preferred modes of injection include dermal, subcutaneous, intramuscular, and locoregional injection. Most preferred are the subcutaneous and intramuscular routes of administration.

Moreover, SFA's exhibit a remarkable wetting and spreading behaviour by which they deliver an incorporated active ingredient rapidly and effectively to the corneal surface and conjunctiva. Wetting means the ability of a liquid to establish and maintain contact with a solid surface, resulting from intermolecular interactions when the two are brought together. The balance between adhesive and cohesive forces determines the degree of wetting. The higher the adhesive forces compared to the cohesive forces, the more a drop of liquid will spread across the surface of the solid material. Conversely, very high cohesive forces within the liquid will cause the drop to form a sphere, thus avoiding contact with the surface. Similarly, spreading may also occur at the interface of two liquids which are brought into contact with each other.

A measure for wetting and spreading is the contact angle θ. The contact angle is the angle at which the liquid-vapour interface meets the solid-liquid or liquid-liquid interface. The tendency of a drop to spread out increases as the contact angle decreases. Thus, the contact angle provides an inverse measure of wettability.

A low contact angle of less than 90° indicates high wettability and/or spreading, whereas a higher contact angle indicates poor wettability and spreading. Perfect wetting and spreading results in a contact angle of 0°, also reported as no measurable contact angle.

The inventors have found that the SFA's used in the present invention, in particular the preferred SFA's, exhibit an excellent wetting of various surfaces which are not easily wetted by conventional drug formulations. For example, the contact angle of both F4H5 and F6H8 on tablets compressed from either trospium chloride or fenofibrate (150 mg of drug substance compressed at 15-20 kN to tablets of 13 mm in diameter) was not measurable, i.e. perfect wetting occurred. It is noted that fenofibrate is an example of a hydrophobic, poorly water-soluble compound, whereas trospium chloride is hydrophilic and water-soluble. In comparison, the contact angle of purified water on the fenofibrate tablet was determined as 92.5°, i.e. the tablet was poorly wetted by water.

A further surprising advantage of SFA's found by the inventors is that they appear to form very small droplets when dispensed from a dropper such as an eye dropper. Without wishing to be bound by theory, it is believed that the small droplet size is a result of an interplay of the SFA's unique properties in terms of their density, viscosity, and surface tension. In any case, it is believed that for topical administration into an eye a small drop or volume of administration is highly advantageous as the capability of the lacrimal sac to accept and hold fluid is extremely limited. In fact, it is very common that the administration of a conventional eye drop formulation based on water or oil immediately leads to a discharge of a substantial fraction of the administered medicine as well as some tear fluid. At the same time, there is a risk that some of the administered dose will be taken up systemically via the nasolacrimal duct. Hence, if an effective dose of an active ingredient can be incorporated in a small volume of liquid which can be dispensed as a very small droplet, this should also contribute to a substantially increased dosing reliability and reproducibility, thus enhancing the safety and effectiveness of the therapy.

A yet further advantage of the invention which is based on the use of SFA's is that they can be designed or mixed for an optimally adjusted evaporation behaviour after administration. Thus it is possible to formulate an ophthalmic composition which delivers an active compound efficiently to the eye in such a way that the liquid vehicles is subsequently eliminated via evaporation. This is in sharp contrast to oily or perfluorinated eye drop vehicles which do easily not evaporate and thus form non-physiological residues at the site of administration, e.g. in the lacrimal sac.

Moreover, the invention provides a means of formulating non-aqueous ophthalmic compositions which are microbiologically stable. This is due to the fact that SFA's are not normally prone to microbial contamination. Hence, it is possible to formulate preservative-free ophthalmic compositions which are better tolerable for many patients, in particular patients suffering from an ophthalmic disease or condition. The same benefit is achieved when the suspensions are used for parenteral injection.

Preferably, the SFA-based suspensions of the invention are used to formulate active ingredients which are either poorly water-soluble or sensitive to hydrolytic degradation, or both. It is believed that the invention is particularly useful if the active compound is selected from poorly water-soluble drug substances which are otherwise challenging to formulate for ophthalmic or injectable use. As used herein, a compound is poorly water-soluble if it exhibits a solubility falling into the definitions of "sparingly soluble", "slightly soluble", "very slightly soluble", or "practically insoluble" (according to Ph. Eur. 6th Ed.). Particularly preferred are active ingredients which are "very slightly soluble" or "practically insoluble". In another embodiment, it is preferred that the active ingredient exhibits a water solubility of less than about 1 mg per mL, as measured at room temperature (between 15 and 25° C.) and at neutral pH (pH 6.0 and pH 8.0).

Examples of suitable active ingredients include poorly soluble antibiotic agents such as ofloxacin, ciprofloxacin, levofloxacin, lomefloxacin, moxifloxacin, gentamycin, tobramycin, chloramphenicol, polymyxin B, neomycin, kanamycin, erythromycin, or fusidic acid; poorly soluble antifungal agents such as amphotericin B; poorly soluble corticoids such as fluorometholone, prednisolone, or dexamethasone; poorly soluble non-steroidal anti-inflammatory agents such as ibuprofen, indometacine, or flurbiprofene; or poorly soluble antiviral agents such as ganciclovir, to mention only a few of the potential drug candidates.

The active ingredient is incorporated in the form of suspended solid particles. In a particular embodiment, the suspended particles largely or exclusively consist of the active ingredient. In another embodiment, the active ingredient is associated with, or embedded in, a solid material which also does not dissolve in the continuous liquid phase of the suspension.

The particle size of the dispersed phase is preferably below about 300 μm, which means that most of the particles, e.g. at least about 90% thereof, have a size in this range. Which type of particle diameter is considered as particle size will depend on the method use for particle size distribution, which in turn is selected to be appropriate for the type of solid material and the approximate size range. For example, laser diffraction or dynamic light scattering (also known as photon correlation spectroscopy or quasi-elastic light scattering) are appropriate methods for determining particle sizes in the colloidal and low micron range, whereas sedimentation analysis, sieve analysis or photoanalysis may be selected for larger particle sizes.

In a further embodiment, at least about 90% of the suspended particles have a size of not more than about 200 μm, in particular from about 0.2 μm to about 200 μm, or from about 0.5 μm to about 150 μm, or from about 1 μm to about 100 μm. Especially for ophthalmic administration, it may also be useful to select micronised material whose predominant particle size is in the range from about 1 μm to about 20 μm, with mean (volume average) particle sizes e.g. in the range from about 2 μm to about 15 μm, as measured by laser diffraction, and in particular from about 2 μm to about 10 μm.

As mentioned, the advantageous effects of the invention are particularly obvious when an active ingredient is selected which is poorly water-soluble and/or sensitive to water, e.g. prone to hydrolytic degradation. Especially in combination with such labile active ingredient it is recommended that the composition is substantially free of water, perhaps except for the residual amounts of water which may be introduced via the solid or liquid components. At the same time, water-free suspensions may also be useful in many other cases.

In contrast to some other suspensions known in prior art, the formulations of the invention require no surfactant, or only small amounts of surfactant, for their physical stabilisation. This is a significant advantage as surfactants have a substantial potential for irritation and local toxicity, especially when administered to the eye or by injection. According to one of the preferred embodiments, the compositions of the invention are substantially free of surfactant. In a further embodiment, the total amount of surfactant or surfactants, if more than one surfactant is incorporated, is not more than about 10 wt.-%, in particular not more than about 5 wt.-%, or preferably not more than about 2 wt.-%, respectively. In further preferred embodiments, the amount is not more than about 1 wt.-%, or not more than about 0.5 wt.-%, respectively.

In this context, the SFA's as described herein, although they possess some amphiphilic properties due to their chemical structure which includes fluorinated and non-fluorinated alkyl (or alkylene) groups characterised by different degrees of lipophilicity, are not understood as being within the scope of surfactants.

The surfactants which are absent or only present in small amounts include non-ionic, cationic, anionic, and zwitterionic surfactants as commonly used as excipients in various types of pharmaceutical compositions, e.g. as wetting agents, emulsifiers, dispersing agents, solubilisers and the like. Examples of surfactants which are considered potentially useful include tyloxapol, poloxamers such as Pluronic F68LF or Lutrol F68, Pluronic L-G2LF and Pluronic L62D, polysorbates such as polysorbate 20 and polysorbate 80, polyoxyethylene castor oil derivatives, sorbitan esters, polyoxyl stearates, lecithins, purified or synthetic phospholipids, and mixtures of two or more thereof.

The compositions of the invention may further comprise a non-fluorinated organic liquids, for example in order to modify the properties of the liquid vehicle, such as the viscosity. Such other liquid may be an oil selected from glyceride oils, liquid waxes, and liquid paraffin, or an organic solvent exhibiting a high degree of biocompatibility, or a mixture of more than one liquid excipients.

Examples of potentially useful oily excipients which may be used in combination with one or more SFA's include triglyceride oils (i.e. soybean oil, olive oil, sesame oil, cotton seed oil, castor oil, sweet almond oil), mineral oil (i.e. petrolatum and liquid paraffin), medium chain triglycerides (MCT), oily fatty acids, isopropyl myristate, oily fatty alcohols, esters of sorbitol and fatty acids, oily sucrose esters, or any other oily substance which is physiologically tolerated by the eye.

Examples of potentially useful organic solvents include glycerol, propylene glycol, polyethylene glycol, and ethanol. However, the concentration of the cosolvent should preferably be low relative to that of the SFA or SFA mixture. If an organic solvent such as ethanol is used, it is recommendable to keep it below a level of approx 5 wt.-%. More preferably, the content of ethanol is from about 0.1 to about 2 wt.-%, and most preferably not more than about 1 wt.-%.

The composition may of course comprise further pharmaceutical excipients as required or useful. Potentially useful excipients include acids, bases, antioxidants, stabilisers, synergists, coloring agents, thickening agents, and—if required in a particular case—a preservative.

Furthermore, the invention provides a pharmaceutical kit comprising the composition as described above and a container holding the composition. Preferably, the container which contains the composition has a dispensing means such as a dropping device adapted for topically administering the composition to the eye of a patient. In one of the preferred embodiments, the dispensing means is adapted to dispense the composition dropwise in volumes of less than about 30 µl per drop. In further embodiments, the dispensing means is adapted to dispense drops having a volume of less than about 20 µl, 15 µl, or 10 µl, respectively. In particular, drop volumes of less than 10 µl are presently considered very useful in view of the limited holding capacity of one of the preferred sites of administration, the front of the eye. For the avoidance of doubt, such small droplet sizes are primarily enabled by the incorporation of the SFA (or SFA's) according to the invention, and common droppers for eye drops which normally deliver aqueous drops of about 30 to 60 µl are capable of dispensing much smaller drops of SFA-based formulations.

The liquid suspensions of the invention may be prepared by conventional methods. In principle, the solid particles comprising the active ingredient may be dispersed in the liquid vehicle comprising the SFA. Alternatively, the particles may be precipitated in situ by adding a—typically organic—solution of the active ingredient (and, optionally, one or more solid excipients) under controlled conditions to the SFA-based vehicle.

The particle size of the dispersed phase may be adjusted before or after the particles are combined with the liquid vehicle. In one of the preferred embodiments, particles of the active ingredient are provided which already have the appropriately selected particle size. Powders having such selected particle size may be obtained directly from the synthesis of the respective compound by crystal engineering, or after synthesis by conventional grinding or milling methods using standard equipment such as a ball mill, hammer mill, roller mill, colloidal mill, jet mill, or the like. If the particle size is to be reduced after preparation of a suspension, ultrasonication as well as various types of homogenisers may be used, such as colloid mills or high pressure homogenisers.

The following examples serve to illustrate the invention; however, these are not to be understood as restricting the scope of the invention.

EXAMPLES

Example 1

The droplet size of selected SFA's in terms of weight and volume of droplets from three droppers was determined and compared to that of purified water. The devices used for dispensing the droplets were (a) a 2 mL Pasteur pipette (wall thickness 0.53 mm; external tip diameter: 1.50 mm; length: 150 mm) made of glass, (b) a 20 G (0.9 mm×50 mm) injection needle, and (c) a dropper from a commercial eye drops product (Hylo-Vision). The droplet weights were measured at 25° C. using a laboratory balance; the volumes were calculated. Each test was performed 10 times. The results of the experiments (mean values of droplet sizes and standard deviations) are shown in table 2.

TABLE 2

| Material | Glass pipette | | Injection needle | | Eye dropper | |
|---|---|---|---|---|---|---|
| | mg | μL | mg | μL | mg | μL |
| Water | 31.2 ± 1.4 | 31.3 ± 1.4 | 11.0 ± 0.9 | 11.1 ± 0.9 | 36.0 ± 2.2 | 36.1 ± 2.2 |
| F4H5 | 6.0 ± 0.4 | 4.7 ± 0.3 | 2.6 ± 0.4 | 2.0 ± 0.3 | 12.4 ± 0.2 | 9.6 ± 0.2 |
| F6H8 | 6.6 ± 0.6 | 5.0 ± 0.4 | 3.4 ± 0.2 | 2.5 ± 0.1 | 13.7 ± 0.4 | 10.3 ± 0.3 |

Table 2 shows that droplets of F4H5 and F6H8 are dramatically smaller and lighter than water droplets dispensed from the same device. Taking into account the fact that SFA's have a high capacity to dissolve many active ingredients very well, it is concluded that SFA's are highly suitable liquid vehicles for eye drops which are better retained by the lacrimal sac, produce little spill-over, and thus have a potential to deliver a dose more reliably and reproducibly to the eye than conventional eye drop formulations.

Example 2

The physiological tolerability of F4H5 and of a mixture of 1 wt.-% ethanol in F4H5 was evaluated in an ex-vivo eye irritation test (EVEIT) using rabbit eyes taken from freshly sacrificed animals. The eyes were fastened in chambers coupled micropump systems which continuously supplied the eyes with cultivation medium (Minimal Essential Medium, MEM T031-05) without fetal calf serum. The vitality of the eyes was monitored by regularly measuring the concentration of lactate and glucose in the chamber eluate. The corneal surface of the eyes was damaged by abrasion, using a dental ceramic abrasive (638XF, Meisinger). For each eye, four lesions of 3.0 to 4.5 mm$^2$ were prepared.

To evaluate the effect of F4H5 and F4H5 with 1 wt.-% ethanol on the cornea, an amount of approx. 0.25 to 0.50 μl of the respective test substance was dropped onto the centre of a cornea once every hour over a period of 12 hours, followed by a 12 hour resting period in which the cornea was submersed in culture medium to simulate a closed lid during a night phase. In addition, an aqueous solution of hyaluronic acid (0.1 wt.-%) was used as reference (hyaluronic acid is know to enhance the restoration of the corneal surface after damage), culture medium was used as control, and aqueous benzalkonium chloride solution (0.01 wt.-%) was used as negative control. Each test was performed over a period of 3 days. The effects were observed by optical coherence tomography (OCT), by digitally determining the dimensions of the lesions after staining with fluorescein, and finally by a histological evaluation of the corneal epithelium and endothelium at the end of each experiment.

In result, it was found that in particular F4H5 was better tolerated than culture medium, and that it exhibits a positive effect on the healing of damaged cornea similar to that of hyaluronic acid. Even when comprising 1 wt.-% of ethanol, F4H5 is tolerated very well by the eye. OCT imaging revealed no indication of penetration of F4H5 into the cornea.

In more detail, it was found that the lesions prepared by abrasion became smaller or larger over time depending on the liquid that was administered to the cornea. Substantial healing occurred when F4H5, F4H5 with 1 wt.-% ethanol, or hyaluronic acid was used. In marked contrast, benzalkonium chloride administration lead to a rapid growth of the lesions eventually leading to a complete disintegration of the corneal epithelium. Culture medium had an intermediate effect. Tables 3 and 4 shows the dimensions of the lesions [mm$^2$] before and after the tests with the various test liquids and controls, respectively.

TABLE 3

| | F4H5 | | | F4H5 + 1% EtOH | |
|---|---|---|---|---|---|
| | Run 1 | Run 2 | Run 3 | Run 1 | Run 2 |
| Initial size [mm$^2$] | 9.95 | 12.88 | 12.09 | 14.68 | 14.99 |
| Final size [mm$^2$] | 0.19 | 1.01 | 0.06 | 0.30 | 2.26 |
| Change [%] | −98.1 | −99.0 | −99.5 | −98.0 | −84.9 |

*EtOH: ethanol

TABLE 4

| | HA | | | MEM | | | |
|---|---|---|---|---|---|---|---|
| | Run 1 | Run 2 | Run 3 | Run 1 | Run 2 | Run 3 | BAC |
| Initial size [mm$^2$] | 13.22 | 16.03 | 14.87 | 15.5 | 15.57 | 13.11 | 16.05 |
| Final size [mm$^2$] | 0.36 | 0.24 | 0.00 | 2.51 | 6.83 | 0.00 | >60 |
| Change [%] | −97.3 | −98.5 | −100 | −83.8 | −56.1 | −100 | ** |

*HA: hyaluronic acid;
BAC: benzalkonium chloride;
MEM: minimal essential medium
** Lesion essentially covered the complete corneal surface Morphological and histological evaluation revealed that the corneas treated with F4H5 or hyaluronic acid had not only healed very well, but were also entirely clear at the end of the tests, with healthy and smooth surface morphology. Eyes treated with F4H5 with 1 wt.-% ethanol showed a healthy overall morphology, the corneas were clear and the epithelia revealed only very minor signs of damage remaining from the lesions. In contrast, some of the controls treated with culture medium showed significant surface roughness, and the eye treated with benzalkonium chloride showed not only the complete disintegration of the corneal epithelium, but also a major impairment of the complete cornea even including the endothelium.

Example 3

In a similar set of experiments as described in Example 2, the physiological tolerability of F6H8 and of a mixture of 1.0 wt.-% ethanol in F6H8 were evaluated in an ex-vivo eye irritation test (EVEIT). Again, minimal essential medium (MEM) was included as negative control, benzalkonium chloride solution (0.01%) as positive control, and hyaluronic acid solution (0.1%) as a reference.

In result, control treatment with MEM lead to a complete remission of the abrasions (starting size: 14.14 mm$^2$) within 2 days, whereas the treatment with BAC increased the lesions from 11.23 mm$^2$ to a complete epithelial loss affecting all of the corneal surface. In the case of hyaluronic acid, the area of corneal damage started with 12.16 mm$^2$ and was reduced within 3 days to only 0.32 mm$^2$ in a first set of experiments, representing a reduction by 97.4%. In a second set, complete healing was achieved with this reference compound. In two separate sets for each test, both F6H8 as well as the mixture of ethanol (1.0%) in F6H8 also lead to a complete remission of the corneal lesions of 10.54 to 16.65 mm$^2$ in size after 2 or 3 days of exposure, respectively, indicating an excellent ophthalmic compatibility.

Example 4

The grinding jar of a laboratory-size planetary ball mill was filled with 8 ml of a suspension of various amounts of crude ciprofloxacin in F6H8 or F4H5, respectively. The mixtures were processed until fine, homogeneous suspensions with particle sizes predominantly below 50 μm were obtained. The densities of the suspensions were determined as 1.327 g/cm$^3$ (ciprofloxacin/F6H8; 3 mg/ml) and 1.286 g/cm$^3$ (ciprofloxacin/F4H5; 3 mg/ml), respectively.

The spreading behaviour of the ciprofloxacin/F6H8-suspension was determined by placing an amount of 50 μL of the suspension onto a clean, plane glass plate. It was observed that the suspension spread evenly; almost the complete wetted area of the glass surface also exhibited active ingredient particles. In other words, not only the liquid phase of the suspension shows an excellent spreading behaviour, but the suspension as such, including the dispersed solid phase.

The dynamic viscosity of ciprofloxacin/F6H8-suspensions was determined for various concentrations of ciprofloxacin. In result, the viscosities at concentrations of 0, 1, 3, and 5 mg/ml were all in the range from about 3.4 to 3.6 mPa·s; only at concentrations of 10 and 20 mg/ml, the viscosity increased moderately to 3.8 and 4.1 mPa·s, respectively, indicating that the suspension will be easily dispensable with conventional droppers or similar devices even at relatively high concentrations of the active ingredient.

Example 5

In a similar manner as described in Example 4, suspensions were prepared from crude levofloxacin, ganciclovir sodium, chlorhexidine and N-octanoyl dopamine in F4H5 or F6H8 having various concentrations of the active ingredients in the range from 1.5 mg/ml to 40 mg/ml were prepared. The suspensions were physically stable. Those in which the dispersed phase settled or creamed over time were readily redispersible by gentle shaking. Excellent spreading behaviour was observed, in particular for the suspensions based on F6H8.

Example 6

A solution of 10 mg of dexamethasone in absolute ethanol was slowly dripped into 10 ml of F6H8 under stirring and at room temperature. Subsequently, the mixture was cooled with ice and ultrasonicated for 40 seconds (Hielscher, UP400S, 100% amplitude). Next, the ethanol was evaporated under vacuum using a rotary evaporator. A fine suspension was obtained whose particle size distribution was determined by laser diffraction (HELOS, Sympatec GmbH). In result, the volume mean diameter (VMD) was 12.20±0.17 m; the corresponding percentile diameters indicating the dimensions below which lie the diameters of 10%, 50% and 90% of the particles, were 2.52±0.03 μm ($X_{10}$), 10.28±0.11 μm ($X_{50}$) and 24.35±0.38 μm ($X_{90}$).

Example 7

The grinding jar (steel, volume: 25 ml) of a laboratory-size planetary ball mill (Retsch, PM100) was filled with 80 grinding balls (steel, diameter; 3 mm), 24 mg of crude ciprofloxacin and 8 ml of F6H8. The mixture was processed for 3 h at 480 rpm, during which the direction of rotation was switched every 10 minutes. Thus a fine suspension was obtained whose particle size distribution was determined by laser diffraction (HELOS, Sympatec GmbH). The volume mean diameter (VMD) was 11.85±0.24 μm, $X_{10}$ was 2.70±0.06 μm, $X_{50}$ was 9.16±0.15 μm, and $X_{90}$ was determined as 25.05±0.55 μm.

As a control, a suspension of 24 mg of crude ciprofloxacin in 8 ml of perfluorooctane (PFO) was prepared using the same procedure. The respective particle size distribution parameters were 11.81±0.07 μm (VMD), 1.64±0.01 μm ($X_{10}$), 10.07±0.05 μm ($X_{50}$), and 24.11±0.11 μm ($X_{90}$). The particle size distributions of both suspensions are also depicted in FIG. 1.

Figure 3:
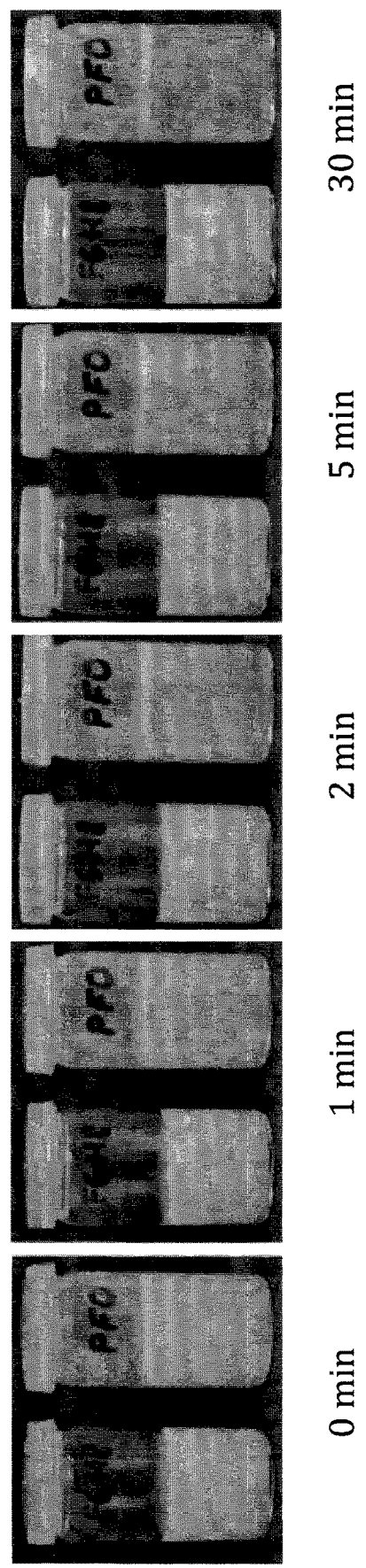
FIG. 3: Images of ciprofloxacin/F6H8 and ciprofloxacin/PFO suspensions at 0 to 30 minutes after shaking.

The two suspensions showed a remarkably different physical stability and behaviour upon vigorous shaking. While the suspension according to the invention (comprising F6H8) remained finely dispersed and substantially homogeneous for at least 30 minutes after shaking, the PFO-based suspension became visibly inhomogeneous within the first 60 seconds after shaking, and the solid particles apparently aggregated and floated as a distinct layer on the liquid phase starting from about 2 minutes after shaking (see FIG. 3).

Example 8

Figure 2:
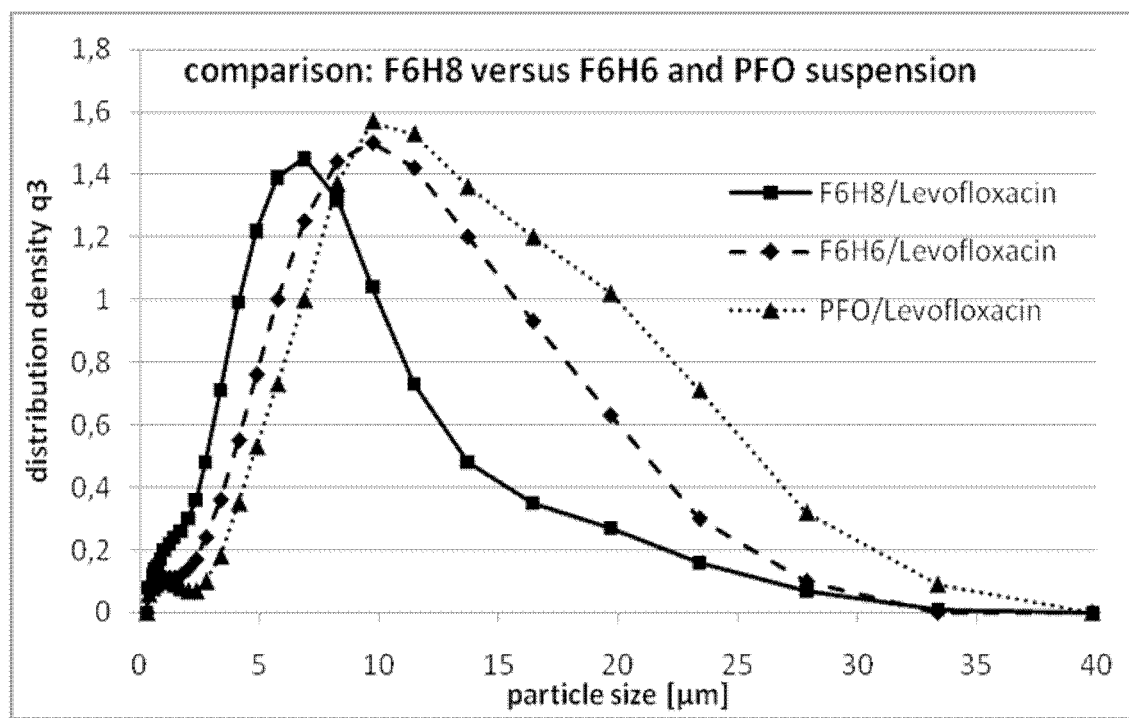
FIG. 2: Particle size distributions of suspensions of levofloxacin in F6H6, F6H8 and PFO.

In a similar procedure as in Example 7, suspensions of levofloxacin (40 mg in 8 ml) in each of F6H6, F6H8 and perfluorooctane (PFO), respectively, were prepared, except that the processing time was 12 hours for each batch. Again, fine suspensions were obtained whose particle distribution parameters are given in table 5 below. The particle size distributions of the suspensions are also depicted in FIG. 2.

Figure 4:
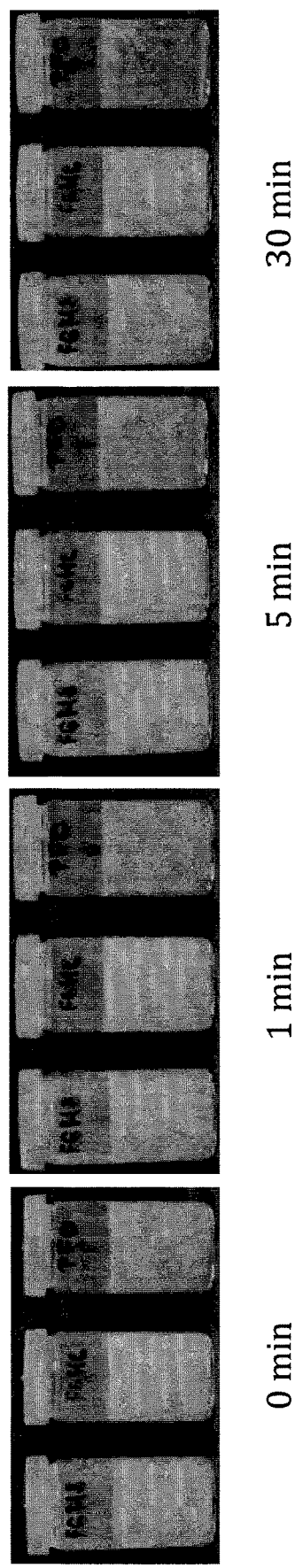
FIG. 4: Images of levofloxacin/F6H6, levofloxacin/F6H8, and levofloxacin/PFO suspensions at 0 to 30 minutes after shaking.

Again, the suspensions differed remarkably from each other with respect to their physical stability and behaviour upon vigorous shaking. While the suspensions according to the invention (comprising F6H6 and F6H8) remained finely dispersed and substantially homogeneous for at least 30 minutes after shaking, the PFO-based suspension became visibly inhomogeneous within second. The solid particles in the PFO-based suspension aggregated rapidly and assembled as a distinct floating layer on the liquid phase starting from about 5 minutes after shaking (see FIG. 4).

TABLE 5

| | Liquid phase | | | |
|---|---|---|---|---|
| | $X_{10}$ [µm] | $X_{50}$ [µm] | $X_{90}$ [µm] | VMD |
| F6H8 | 1.33 ± 0.01 | 5.76 ± 0.02 | 12.75 ± 0.17 | 6.69 ± 0.04 |
| F6H6 | 2.28 ± 0.02 | 8.41 ± 0.04 | 17.15 ± 0.16 | 9.22 ± 0.07 |
| PFO | 3.49 ± 0.13 | 10.24 ± 0.07 | 20.84 ± 0.19 | 11.35 ± 0.10 |

Example 9

In order to evaluate the biological activity of suspended active ingredients in SFA's, suspensions of ciprofloxacin, tobramycin, and gentamycin, each individually and separately suspended in F4H5 or F6H8, respectively, were prepared and tested in an agar diffusion test according to Clinical and Laboratory Standards Institute (CLSI). Commercially available standard filter paper disks loaded with 5 µg of ciprofloxacin were compared to filter paper disks soaked with 1.66 µL of a suspension of ciprofloxacin (3 mg/mL) in F4H5 or F6H8, respectively. Similarly, standard filter paper disks loaded with 10 µg of tobramycin were compared to disks soaked with 3.3 µL of a suspension of tobramycin (3 mg/mL) in F4H5 or F6H8, respectively; and standard filter paper disks loaded with 10 µg of gentamycin were compared to disks soaked with 3.3 µL of a suspension of gentamycin (3 mg/mL) in F4H5 or F6H8, respectively. The disks were placed on agar culture plates (agar type MH) innoculated with *Staphylococcus aureus, Escherichia coli* or *Pseudomonas aeruginosa*, respectively, and incubated. In result, it was found that the inhibition zones around the disks differed substantially between the various active compounds and also between test germs with inhibition zones ranging from 16 to 40 mm, whereas there was no substantial difference between the standard disks and the corresponding disks loaded with the experimental suspensions of the same active compound (inhibition zones mostly differing by about 2 or 3 mm only). Thus it is clear that the suspensions according to the invention retain the biological activity of the incorporated drug substances.

The invention claimed is:

1. A pharmaceutical composition in the form of a suspension comprising a dispersed phase in a liquid continuous phase wherein:

(a) the dispersed phase comprises solid particles of an active ingredient, said active ingredient is selected from the group consisting of antibiotic agents, antifungal agents, corticoid, non-steroidal anti-inflammatory agents, and antiviral agents, said active ingredient being present in a therapeutically effective amount, and (b) the liquid continuous phase comprises a liquid vehicle comprising a semifluorinated alkane of formula RFRH, wherein RF is a linear perfluorinated hydrocarbon segment with 3 to 10 carbon atoms, and wherein RH is a linear alkyl group with 3 to 10 carbon atoms;

wherein the composition is substantially free of water, and wherein the particles of the active ingredient have a volume mean diameter as measured by laser diffraction of not more than 15 µm.

2. The composition of claim 1, wherein the particles of the active ingredient have a volume mean diameter as measured by laser diffraction of about 2 to about 10 µm.

3. The composition of claim 1, wherein the active ingredient is an antibiotic agent selected from ofloxacin, ciprofloxacin, levofloxacin, lomefloxacin, moxifloxacin, gentamycin, tobramycin, chloramphenicol, polymyxin B, neomycin, kanamycin, erythromycin, and fusidic acid.

4. The composition of claim 1, wherein the active ingredient is the antifungal agent amphotericin B.

5. The composition of claim 1, wherein the active ingredient is a corticoid selected from fluorometholone, prednisolone, and dexamethasone.

6. The composition of claim 1, wherein the active ingredient is an anti-inflammatory agent selected from ibuprofen, indomethacin, and flurbiprofen.

7. The composition of claim 1, wherein the active ingredient is the anti-viral agent ganciclovir.

8. The composition of claim 1, wherein the suspension remains substantially homogenous and finely dispersed for at least 30 minutes after shaking.

9. The composition of claim 1, being substantially free of a surfactant.

10. The composition of claim 1, wherein the composition comprises a total amount of surfactant of not more than about 5 wt.-%.

11. The composition of claim 1, wherein the active ingredient is a poorly water-soluble drug substance and/or sensitive to hydrolytic degradation.

12. The composition of claim 1, wherein the active ingredient exhibits a water solubility of less than about 1 mg per ml, as measured at room temperature and neutral pH.

13. The composition of claim 1, wherein the semifluorinated alkane is selected from F4H5 and F6H8.

14. The composition of claim 1, wherein the composition is adapted for topical ophthalmic administration to an eye of a patient.

15. The composition of claim 1, wherein the semifluorinated alkane is selected from F4H5, F4H6, F6H6 and F6H8.

16. A pharmaceutical composition in the form of a suspension comprising a dispersed phase in a liquid continuous phase wherein:

(a) the dispersed phase comprises solid particles of an active ingredient, said active ingredient is selected from the group consisting of antibiotic agents, antifungal agents, corticoid, non-steroidal anti-inflammatory agents, and antiviral agents, said active ingredient being present in a therapeutically effective amount, and (b) the liquid continuous phase comprises a liquid vehicle comprising a semifluorinated alkane of formula RFRH, wherein RF is a linear perfluorinated hydrocarbon segment with 3 to 10 carbon atoms, and wherein RH is a linear alkyl group with 3 to 10 carbon atoms;

wherein the composition is substantially free of water, wherein the composition further comprises a non-fluorinated organic liquid, and wherein the particles of the active ingredient have a volume mean diameter as measured by laser diffraction of not more than 15 µm.

17. The composition of claim 16, wherein the non-fluorinated organic liquid is an oil or an organic solvent; optionally wherein the oil is selected from the group consisting of a glyceride oil, a liquid wax or a liquid paraffin.

18. The composition of claim 16, wherein the active ingredient is an antibiotic agent selected from ofloxacin, ciprofloxacin, levofloxacin, lomefloxacin, moxifloxacin, gentamycin, tobramycin, chloramphenicol, polymyxin B, neomycin, kanamycin, erythromycin, and fusidic acid; or a corticoid selected from fluorometholone, prednisolone, and dexamethasone; or an anti-inflammatory agent selected from ibuprofen, indomethacin, and flurbiprofen; or the antifungal agent amphotericin B; or the anti-viral agent ganciclovir.

19. The composition of claim 16, wherein the particles of the active ingredient have a volume mean diameter as measured by laser diffraction of about 2 to about 10 μm.

20. The composition of claim 16, wherein the semifluorinated alkane is selected from F4H5, F4H6, F6H6 and F6H8, or wherein the semifluorinated alkane is selected from F4H5 and F6H8.

21. The composition of claim 1, wherein the semifluorinated alkane has a refractive index in the range of 1.29 to 1.35 at 20° C.

22. The composition of claim 1, wherein the semifluorinated alkane is selected from F4H4, F4H5, F4H6, F4H7, F4H8, F6H4, F6H6, F6H7, F6H8, F6H9, and F6H10.

* * * * *